(12) United States Patent
Czibula et al.

(10) Patent No.: US 7,943,621 B2
(45) Date of Patent: May 17, 2011

(54) SALTS OF PIPERAZINE COMPOUNDS AS $D_3/D_2$ ANTAGONISTS

(75) Inventors: Laszlo Czibula, Budapest (HU); Ferenc Sebok, Mezokovácsháza (HU); Istvan Greiner, Budapest (HU); Gyorgy Domany, Óbánya (HU); Eva Againe Csongor, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 221 days.

(21) Appl. No.: 12/118,437

(22) Filed: May 9, 2008

(65) Prior Publication Data

US 2009/0023750 A1    Jan. 22, 2009

(51) Int. Cl.
*A61K 31/497*    (2006.01)
*C07D 295/00*    (2006.01)
(52) U.S. Cl. .................... 514/252.12; 544/393
(58) Field of Classification Search ............. 514/252.12; 544/393
See application file for complete search history.

(56) References Cited

U.S. PATENT DOCUMENTS 7,737,142 B2 * 6/2010 Againe Csongor et al. ............ 514/235.8
2006/0229297 A1 10/2006 Csongor

OTHER PUBLICATIONS

Berge, et al., Pharmaceutical Salts, J. of Pharm. Sciences (1977).*
Levant, "The D3 dopamine receptor: neurobiology and potential clinical relevance," *Pharmacol. Rev.*, 1997, 49(3):231-252.
Levant et al., *CNS Drugs*, 1999, 12:391-.
Levant and McCarson, "D(3) dopamine receptors in rat spinal cord: implications for sensory and motor function," *Neurosci. Lett.*, 2001, 303:9-12.
Pilla et al., "Selective inhibition of cocaine-seeking behaviour by a partial dopamine D3 receptor agonist," *Nature*, 1999, 400:371-375.
Schwartz et al., "Dopamine D3 receptor: basic and clinical aspects," *Clin. Neuropharmacol.*, 1993, 16(4):295-314.
Sokoloff et al., "Molecular cloning and characterization of a novel dopamine receptor (D3) as a target for neuroleptics," *Nature*, 1990, 347:146-151.
Wong and Van Tol, "Schizophrenia: from phenomenology to neurobiology," *Neurosci. Biobehav. Rev.*, 2003, 27(3):269-306.

* cited by examiner

*Primary Examiner* — James O Wilson
*Assistant Examiner* — Erich A Leeser
(74) *Attorney, Agent, or Firm* — Fish & Richardson P.C.

(57) ABSTRACT

The present invention relates to novel monohydrochloride, dihydrochloride, monohydrobromide, maleate and methanesulphonate salts of trans 4-{2-[4-(2,3-dichlorophenyl)-piperazine-1-yl]-ethyl}-N,N-dimethylcarbamoyl-cyclohexylamine and/or their hydrates and/or solvates. Moreover, the invention relates to the process for preparing the salts and their hydrates and/or solvates, to their use in the treatment and/or prevention of conditions which require modulation of dopamine receptor and to pharmaceutical compositions containing them.

17 Claims, 4 Drawing Sheets

SALTS OF PIPERAZINE COMPOUNDS AS $D_3/D_2$ ANTAGONISTS

CROSS-REFERENCE TO RELATED APPLICATIONS

The present application claims the benefit of Hungarian Application No. HU P0700339, filed on filed May 1, 2007. The disclosure of the prior application is considered part of (and is incorporated by reference in) the disclosure of this application.

TECHNICAL FIELD

The present invention relates to novel salts of trans 4-{2-[4-(2,3-dichlorophenyl)-piperazine-1-yl]-ethyl}-N,N-dimethylcarbamoyl-cyclohexylamine, to processes for their preparation, to pharmaceutical compositions containing them and to their use in the treatment and/or prevention of conditions which require modulation of dopamine receptors.

BACKGROUND

U.S. Patent Publication No. 2006/0229297 discloses (thio)-carbamoyl-cyclohexane derivatives that are $D_3$ and $D_2$ dopamine receptor subtype preferring ligands, having the formula (I):

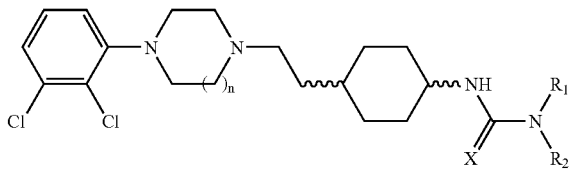

(I)

wherein $R_1$, $R_2$, X, and n are as defined therein. One particular compound disclosed therein is trans-1{4-[2-[4-(2,3-dichlorophenyl)-piperazin-1-yl]-ethyl]-cyclohexyl}-3,3-dimethyl-urea, which is also known as trans-4-{2-[4-(2,3-dichlorophenyl)-piperazin-1-yl]-ethyl}-N,N-dimethylcarbamoyl-cyclohexylamine, the structural formula for which is shown below:

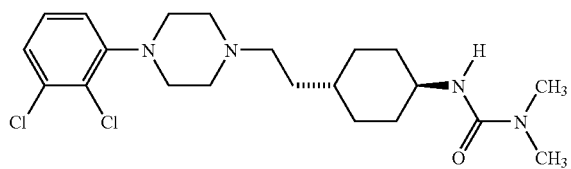

Compounds of formula (I) act as a dopamine receptor antagonists, particularly $D_3/D_2$ receptor antagonists, and are useful in the treatment and prevention of pathological conditions which require modulation of dopamine receptors.

In some cases, an appropriate salt of an active may improve certain properties suitable for pharmaceutical compounds (i.e., stability, handling properties, ease of large scale synthesis, etc.). However, selection of a suitable salt for a particular active agent is not always straightforward, since the properties of salts of different compounds formed with the same salt forming agent may differ greatly. Moreover, formation of particular salts of a compound possessing more than one basic centre may be difficult to achieve in high yield due to formation of multiple products.

SUMMARY

Applicants have surprisingly found that certain salts of trans 4-{2-[4-(2,3-dichlorophenyl)-piperazine-1-yl]-ethyl}-N,N-dimethylcarbamoyl-cyclohexylamine can be prepared in high yield and high purity, and that these salts exhibit suitable solubility, handling and stability characteristics for use in pharmaceutical compositions. The terms "high yield" and "high purity" have the meaning ascribed to them by pharmaceutical industry standards. "High yield" is generally understood to mean a yield of at least 80%. "High purity" is generally understood to mean that the sum of impurities is not greater than 0.5%.

The present invention relates to novel monohydrochloride, dihydrochloride, monohydrobromide, maleate and methanesulphonate salts of trans 4-{2-[4-(2,3-dichlorophenyl)-piperazine-1-yl]-ethyl}-N,N-dimethylcarbamoyl-cyclohexylamine and/or their hydrates and/or solvates, to processes for preparing them, to pharmaceutical compositions containing them and to their use in the therapy and/or prevention of conditions which require modulation of dopamine receptors, e.g., $D_3/D_2$ receptors.

In some embodiments, the salts have one or more properties suitable for successful industrial scale synthesis and/or which may effect the resulting purity of the active agent. In contrast to many crude active agents, in which product is recovered from a reaction mixture by a complicated and often multi-step process, which can decrease yields and cause a substantial increase in production costs, in some embodiments the favourable properties of the salts include one or more of being easy-to handle, stable, and readily isolable (i.e. isolatable). In some embodiments, the salts can include one or more of the aforementioned favourable properties and/or one or more properties that are also considered favourable by the pharmaceutical industry, such as stability and/or purity. The durability of the pharmaceutical composition, which includes the stability of the active agent itself, can be useful for quality control purposes.

DETAILED DESCRIPTION

In one embodiment, the present invention relates to trans 4-{2-[4-(2,3-dichlorophenyl)-piperazine-1-yl]-ethyl}-N,N-dimethylcarbamoyl-cyclohexylamine monohydrochloride, and/or hydrates and/or solvates thereof, for example, trans 4-{2-[4-(2,3-dichlorophenyl)-piperazine-1-yl]-ethyl}-N,N-dimethylcarbamoyl-cyclohexylamine monohydrochloride.

In certain embodiments, the present invention provides a crystalline form of trans 4-{2-[4-(2,3-dichlorophenyl)-piperazine-1-yl]-ethyl}-N,N-dimethylcarbamoyl-cyclohexylamine monohydrochloride (Form I) characterized by a X-ray powder diffraction pattern having characteristic peaks at about 6.6, about 7.3, about 13.2, about 21.1 and about 22.1, each 6±0.2 degrees 2θ. In some embodiments, the crystalline form of trans 4-{2-[4-(2,3-dichlorophenyl)-piperazine-1-yl]-ethyl}-N,N-dimethylcarbamoyl-cyclohexylamine monohydrochloride (Form I) is characterized by a X-ray powder diffraction pattern having characteristic peaks at about 6.6, about 7.3, about 13.2, about 14.2, about 16.9, about 21.1, about 22.4, about 24.8, about 26.5 and about 26.6±0.2 degrees 2θ.

Figure 1:
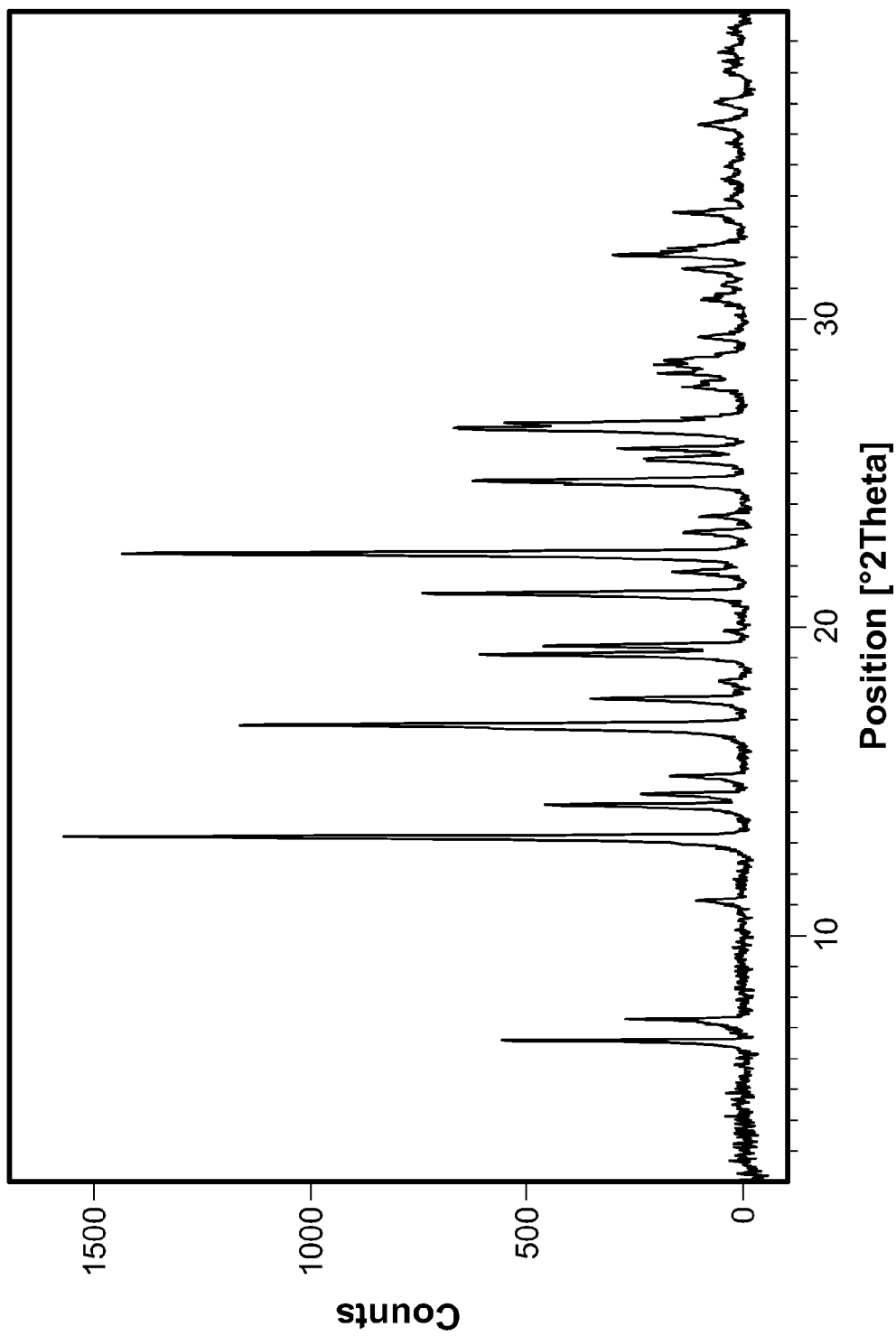
FIG. 1 shows the X-ray powder diffraction pattern of Form I trans-1{4-[2-[4-(2,3-dicholorphenyl)-piperazin-1-yl]-ethyl]-cyclohexyl}-3,3-dimethyl-urea hydrochloride.

In a further embodiment, Form I trans 4-{2-[4-(2,3-dichlorophenyl)-piperazine-1-yl]-ethyl}-N,N-dimethylcarbamoyl-cyclohexylamine monohydrochloride is characterized by a X-ray powder diffraction pattern substantially as shown in FIG. 1. and diffraction peaks given in Table 1.

TABLE 1

| Pos. [°2θ] | d-spacing [Å] | Rel. Int. [%] |
|---|---|---|
| 6.6 | 13.410 | 37.6 |
| 7.3 | 12.124 | 18.1 |
| 11.1 | 7.941 | 6.8 |
| 13.2 | 6.700 | 100.0 |
| 14.2 | 6.222 | 29.8 |
| 14.6 | 6.070 | 15.8 |
| 15.2 | 5.837 | 11.5 |
| 16.7 | 5.262 | 69.1 |
| 16.9 | 5.015 | 22.9 |
| 17.7 | 4.861 | 3.8 |
| 18.3 | 4.643 | 39.6 |
| 19.1 | 4.575 | 29.9 |
| 19.4 | 4.472 | 2.7 |
| 19.9 | 4.211 | 48.5 |
| 21.1 | 4.083 | 10.3 |
| 21.8 | 3.970 | 93.0 |
| 22.4 | 3.853 | 9.4 |
| 23.1 | 3.771 | 6.6 |
| 23.6 | 3.595 | 40.6 |
| 24.8 | 3.496 | 14.9 |
| 25.5 | 3.455 | 19.1 |
| 25.8 | 3.368 | 43.4 |
| 26.5 | 3.350 | 34.1 |
| 26.6 | 3.212 | 7.9 |
| 26.8 | 3.160 | 12.9 |
| 27.8 | 3.113 | 10.4 |
| 28.2 | 3.038 | 6.7 |
| 28.7 | 2.919 | 5.5 |
| 29.4 | 2.875 | 3.0 |
| 30.6 | 2.830 | 8.5 |
| 31.1 | 2.790 | 19.5 |
| 31.6 | 2.679 | 10.7 |
| 32.1 | 2.643 | 2.0 |
| 32.3 | 2.597 | 2.6 |
| 33.5 | 2.474 | 6.3 |
| 33.9 | 2.369 | 2.1 |
| 34.5 | 2.289 | 0.8 |

In other embodiments, Form I trans 4-{2-[4-(2,3-dichlorophenyl)-piperazine-1-yl]-ethyl}-N,N-dimethylcarbamoyl-cyclohexylamine monohydrochloride is characterized by an infrared spectrum having characteristic peaks at about 3321, about 2914, about 1652, about 1526, about 956, about 784 cm−1±4 cm−1. In some embodiments, Form I trans 4-{2-[4-(2,3-dichlorophenyl)-piperazine-1-yl]-ethyl}-N,N-dimethylcarbamoyl-cyclohexylamine monohydrochloride is characterized by an infrared spectrum having characteristic peaks at about 3321, about 2931, about 2914, about 2466, about 1652, about 1526, about 956, about 784 and about 715 cm$^{-1}$±4 cm$^{-1}$.

Figure 2:
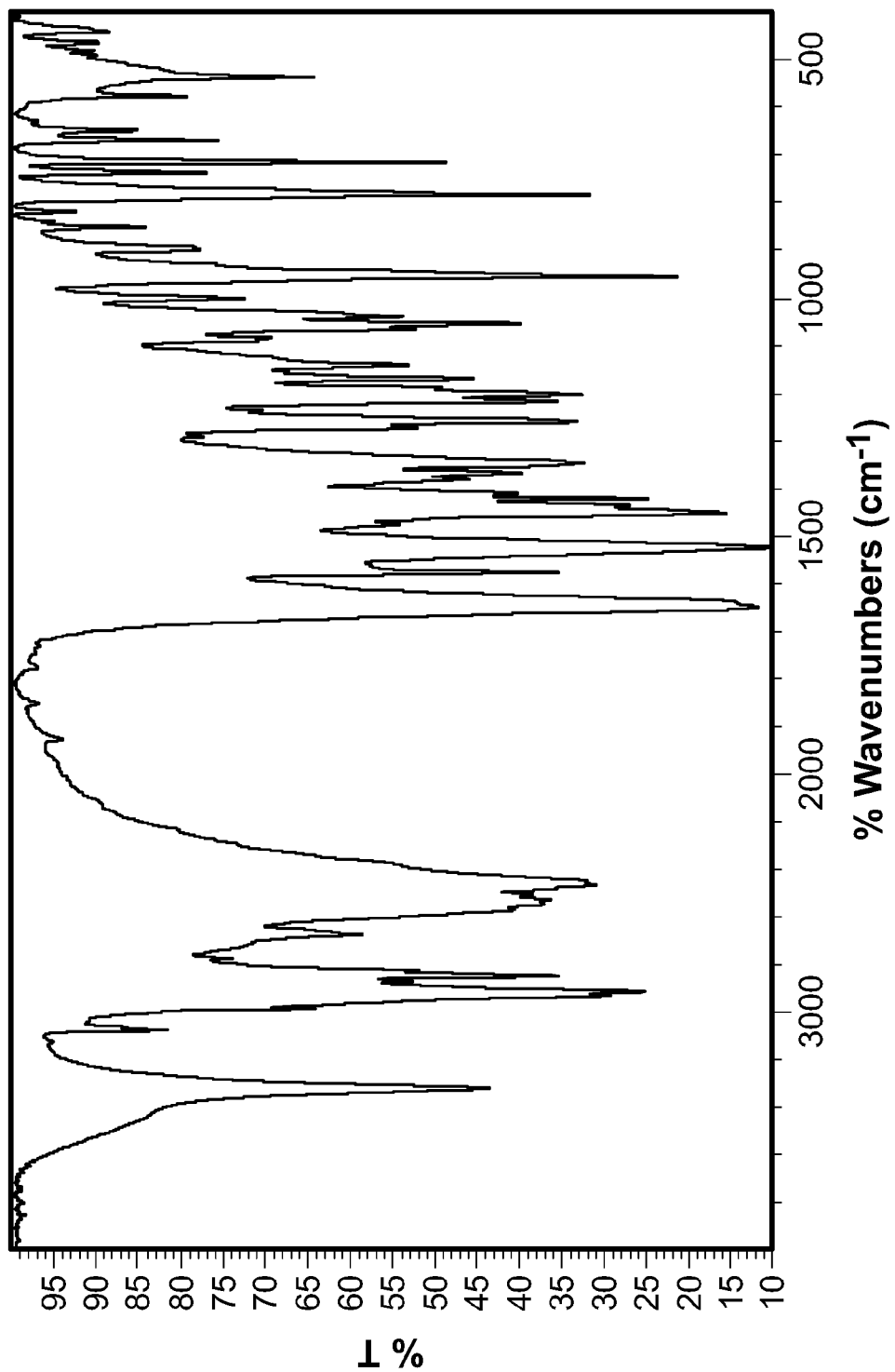
FIG. 2 shows the FT infrared spectrum for Form I trans-1{4-[2-[4-(2,3-dicholorphenyl)-piperazin-1-yl]-ethyl]-cyclohexyl}-3,3-dimethyl-urea hydrochloride.

In one embodiment, Form I trans 4-{2-[4-(2,3-dichlorophenyl)-piperazine-1-yl]-ethyl}-N,N-dimethylcarbamoyl-cyclohexylamine monohydrochloride is characterized by an infrared spectrum substantially as shown in FIG. 2 and IR absorption bands given in Table 2.

TABLE 2

| Peak pos. [cm$^{-1}$] | |
|---|---|
| 441 | 1294 |
| 464 | 1348 |
| 481 | 1370 |
| 536 | 1382 |
| 576 | 1413 |
| 649 | 1423 |
| 669 | 1438 |
| 715 | 1455 |
| 737 | 1476 |
| 784 | 1526 |
| 819 | 1579 |
| 852 | 1652 |
| 900 | 2466 |
| 956 | 2506 |
| 1002 | 2528 |
| 1040 | 2673 |
| 1055 | 2774 |
| 1066 | 2824 |
| 1085 | 2850 |
| 1142 | 2869 |
| 1171 | 2914 |
| 1204 | 2931 |
| 1218 | 2987 |
| 1239 | 3075 |
| 1261 | 3321 |
| 1274 | |

In another embodiment, Form I trans 4-{2-[4-(2,3-dichlorophenyl)-piperazine-1-yl]-ethyl}-N,N-dimethylcarbamoyl-cyclohexylamine monohydrochloride is characterized by a Raman spectrum having characteristic peaks at about 2969, about 2933, about 2850, about 1578, about 1052, about 475 cm−1±4 cm−1. In some embodiments, Form I trans 4-{2-[4-(2,3-dichlorophenyl)-piperazine-1-yl]-ethyl}-N,N-dimethylcarbamoyl-cyclohexylamine monohydrochloride is characterized by a Raman spectrum having characteristic peaks at about 3070, about 2986, about 2969, about 2933, about 2914, about 2864, about 2850, about 1578, about 1458, about 1052, and about 475 cm$^{-1}$±4 cm$^{-1}$.

Figure 3:
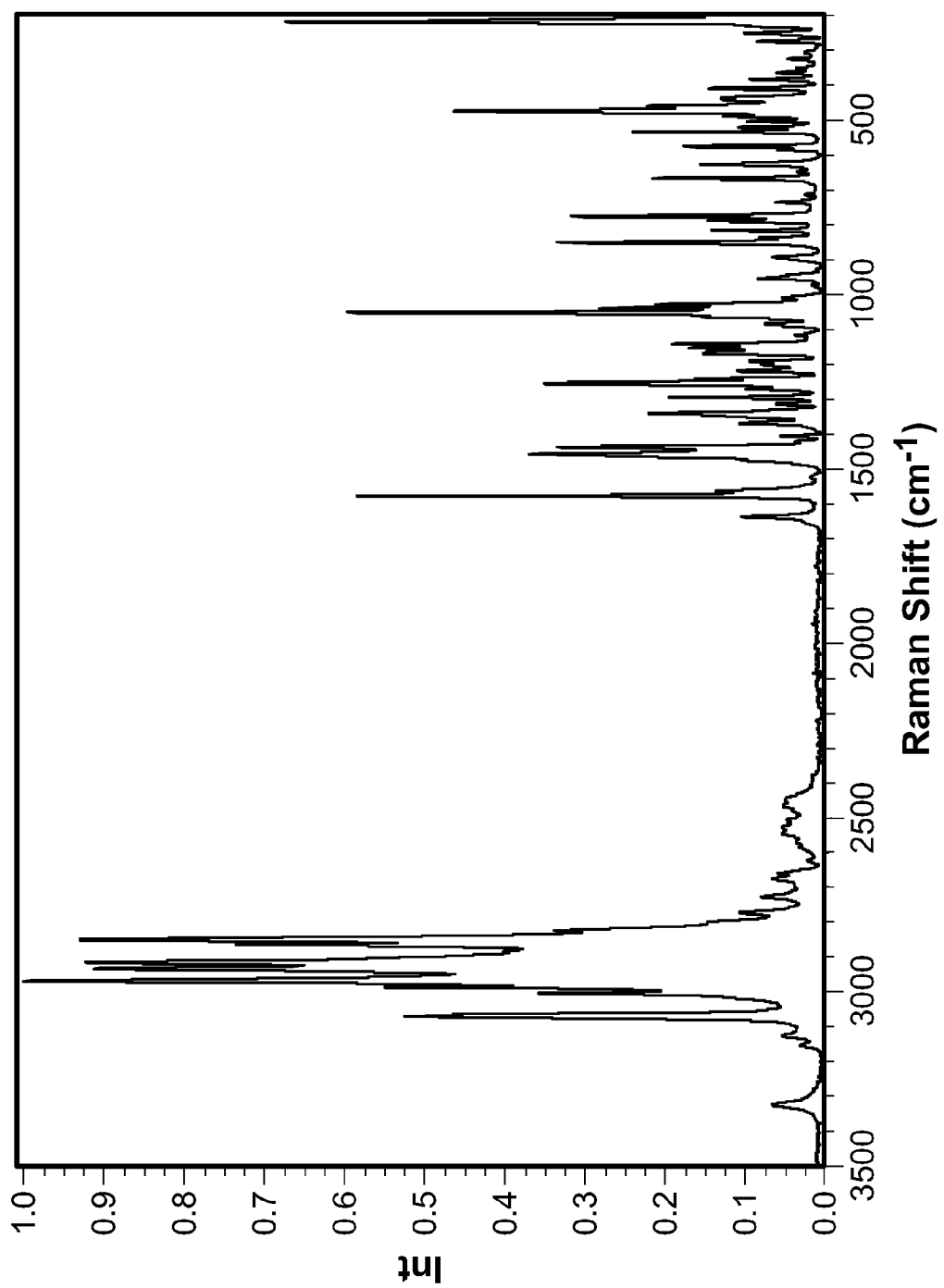
FIG. 3 shows the FT Raman spectrum for Form I trans-1{4-[2-[4-(2,3-dichlorophenyl)-piperazin-1-yl]-ethyl]-cyclohexyl}-3,3-dimethyl-urea hydrochloride.

In another embodiment, Form I trans 4-{2-[4-(2,3-dichlorophenyl)-piperazine-1-yl]-ethyl}-N,N-dimethylcarbamoyl-cyclohexylamine monohydrochloride is characterized by a Raman spectrum substantially as shown in FIG. 3 and Raman peaks given in Table 3.

TABLE 3

| Raman shift [cm$^{-1}$] | |
|---|---|
| 220 | 1170 |
| 252 | 1193 |
| 275 | 1220 |
| 326 | 1241 |
| 366 | 1256 |
| 384 | 1272 |
| 411 | 1296 |
| 439 | 1314 |
| 461 | 1342 |
| 475 | 1371 |
| 490 | 1406 |
| 504 | 1438 |

TABLE 3-continued

| Raman shift [cm$^{-1}$] | |
|---|---|
| 522 | 1459 |
| 535 | 1563 |
| 576 | 1579 |
| 586 | 1638 |
| 628 | 2466 |
| 668 | 2530 |
| 737 | 2676 |
| 777 | 2727 |
| 790 | 2772 |
| 818 | 2824 |
| 839 | 2851 |
| 852 | 2864 |
| 894 | 2914 |
| 956 | 2933 |
| 1010 | 2969 |
| 1030 | 2986 |
| 1040 | 3004 |
| 1052 | 3070 |
| 1085 | 3126 |
| 1143 | 3324 |
| 1154 | |

With respect to the term "substantially," one skilled in the art would understand that the relative intensities of the peaks obtained by X-ray powder diffraction and bands obtained by Infrared or Raman spectroscopy can vary, depending upon the sample preparation technique, the sample mounting procedure and the particular instrument employed. For example, the peak assignments for X-ray powder diffraction patterns can vary by plus or minus about 0.2 degrees 2θ. For Infrared and Raman spectroscopy, the peak assignments may vary by about plus or minus 4 cm$^{-1}$.

Figure 4:
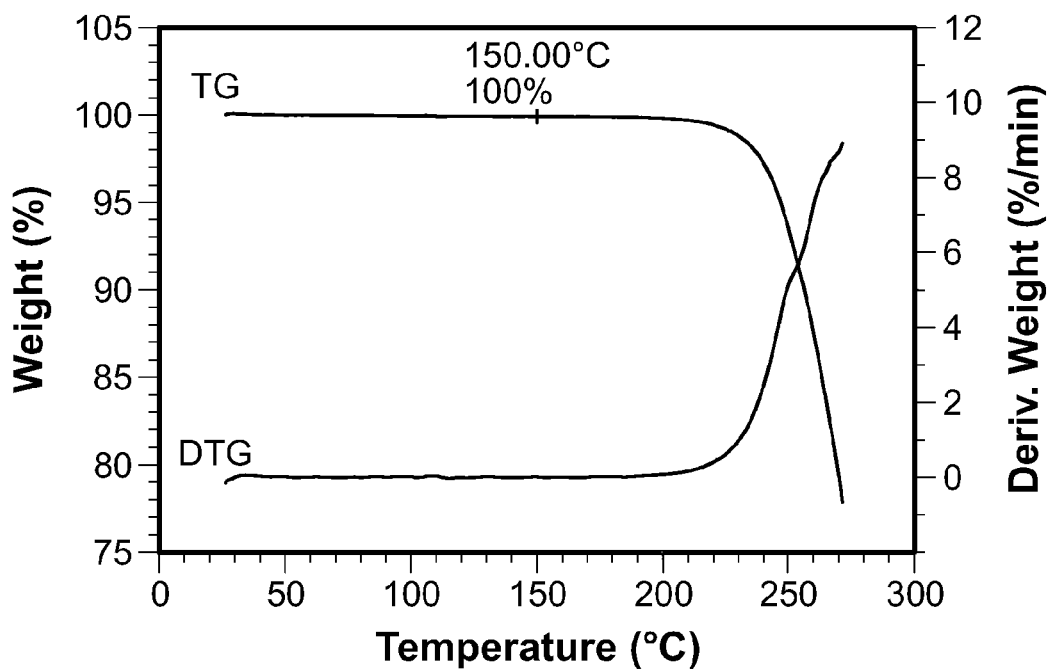
FIG. 4 shows the thermogravimetric analysis for Form I trans-1{4-[2-[4-(2,3-dicholorphenyl)-piperazin-1-yl]-ethyl]-cyclohexyl}-3,3-dimethyl-urea hydrochloride.
Figure 5:
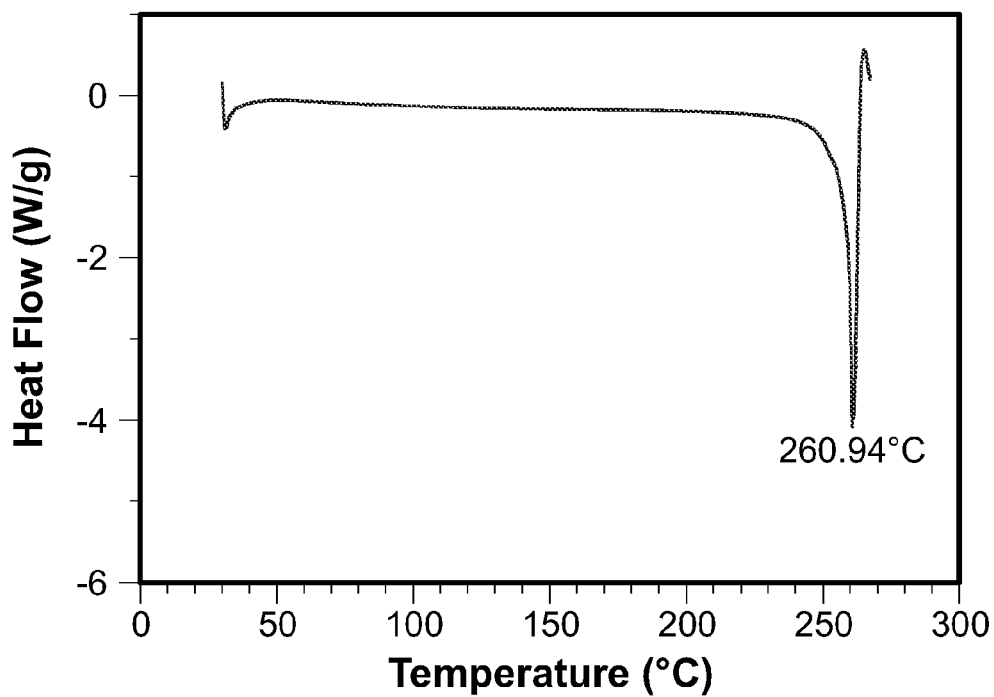
FIG. 5 shows the differential scanning calorimetry trace for Form 111 trans-1{4-[2-[4-(2,3-dicholorphenyl)-piperazin-1-yl]-ethyl]-cyclohexyl}-3,3-dimethyl-urea hydrochloride.

In other embodiments, Form I trans 4-{2-[4-(2,3-dichlorophenyl)-piperazine-1-yl]-ethyl}-N,N-dimethylcarbamoyl-cyclohexylamine monohydrochloride can be identified by its thermogravimetric analysis, such as shown in FIG. 4, or by a differential scanning calorimetry (DSC) trace such as shown in FIG. 5.

In a further embodiment, the present invention relates to trans 4-{2-[4-(2,3-dichlorophenyl)-piperazine-1-yl]-ethyl}-N,N-dimethylcarbamoyl-cyclohexylamine dihydrochloride, and/or hydrates and/or solvates thereof, for example, trans 4-{2-[4-(2,3-dichlorophenyl)-piperazine-1-yl]-ethyl}-N,N-dimethylcarbamoyl-cyclohexylamine dihydrochloride.

In another embodiment, the present invention relates to trans 4-{2-[4-(2,3-dichlorophenyl)-piperazine-1-yl]-ethyl}-N,N-dimethylcarbamoyl-cyclohexylamine monohydrobromide, and/or hydrates and/or solvates thereof, for example, trans 4-{2-[4-(2,3-dichlorophenyl)-piperazine-1-yl]-ethyl}-N,N-dimethylcarbamoyl-cyclohexylamine monohydrobromide.

In yet another embodiment, the present invention relates to trans 4-{2-[4-(2,3-dichlorophenyl)-piperazine-1-yl]-ethyl}-N,N-dimethylcarbamoyl-cyclohexylamine maleate, and/or hydrates and/or solvates thereof, for example, trans 4-{2-[4-(2,3-dichlorophenyl)-piperazine-1-yl]-ethyl}-N,N-dimethylcarbamoyl-cyclohexylamine maleate.

In one embodiment, the present invention relates to trans 4-{2-[4-(2,3-dichlorophenyl)-piperazine-1-yl]-ethyl}-N,N-dimethylcarbamoyl-cyclohexylamine methanesulfonate, and/or hydrates and/or solvates thereof, for example, trans 4-{2-[4-(2,3-dichlorophenyl)-piperazine-1-yl]-ethyl}-N,N-dimethylcarbamoyl-cyclohexylamine methanesulfonate.

The present invention also provides processes for preparing monohydrochloride, dihydrochloride, monohydrobromide, maleate and methanesulphonate salts of trans 4-{2-[4-(2,3-dichlorophenyl)-piperazine-1-yl]-ethyl}-N,N-dimethylcarbamoyl-cyclohexylamine, and/or hydrates and/or solvates thereof.

For example, the monohydrochloride, dihydrochloride, monohydrobromide, maleate and methanesulphonate salts of trans 4-{2-[4-(2,3-dichlorophenyl)-piperazine-1-yl]-ethyl}-N,N-dimethylcarbamoyl-cyclohexylamine may be prepared from trans 4-{2-[4-(2,3-dichlorophenyl)-piperazine-1-yl]-ethyl}-N,N-dimethylcarbamoyl-cyclohexylamine.

In one embodiment, trans 4-{2-[4-(2,3-dichlorophenyl)-piperazine-1-yl]-ethyl}-N,N-dimethylcarbamoyl-cyclohexylamine is added to a suitable solvent or a mixture of solvents (to produce a suspension or a solution), then a desired acid, or a salt of the desired acid prepared by reaction of the acid with a base that is a weaker base than trans 4-{2-[4-(2,3-dichlorophenyl)-piperazine-1-yl]-ethyl}-N,N-dimethylcarbamoyl-cyclohexylamine, or a solution thereof, is added. Optionally, the salt form is isolated, for example by concentrating the reaction mixture, or alternatively, by cooling the reaction mixture (with or without concentrating the mixture first) and isolating the resulting precipitate by filtration. As used herein, the term "isolated" does not require absolute purity, but rather is intended as a relative term. Thus, for example, an isolated compound can be one in which the subject compound is at a higher concentration than in the environment from which it was removed.

In some embodiments for the preparation of trans 4-{2-[4-(2,3-dichlorophenyl)-piperazine-1-yl]-ethyl}-N,N-dimethylcarbamoyl-cyclohexylamine monohydrochloride, trans 4-{2-[4-(2,3-dichlorophenyl)-piperazine-1-yl]-ethyl}-N,N-dimethylcarbamoyl-cyclohexylamine is added to a mixture of methanol/water, then a stoichiometric amount of hydrochloric acid is added. The reaction mixture is then heated to afford a homogenous solution and, after cooling, the product is isolated by filtration.

The monohydrochloride, dihydrochloride, monohydrobromide, maleate and methanesulphonate salts of trans-4-{2-[4-(2,3-dichlorophenyl)-piperazine-1-yl]-ethyl}-N,N-dimethylcarbamoyl-cyclohexyl-amine exhibit excellent stability when stored as aqueous solutions. In some embodiments, the product is stable (for example is still sufficiently within its specifications that it can be used for its intended purpose) for at least about six months. In some embodiments, the product is stable for at least about two years.

The monohydrochloride, monohydrobromide, maleate and methanesulphonate salts of trans-4-{2-[4-(2,3-dichlorophenyl)-piperazine-1-yl]-ethyl}-N,N-dimethylcarbamoyl-cyclohexyl-amine also exhibit excellent stability when stored as in the solid state. In some embodiments, the monohydrochloride salt has the following long term stability: 48 months/25±2° C./60±5% RH. In some embodiments, the monohydrochloride salt has the following accelerated stability: 6 months/40±2° C./75±5% RH.

In some embodiments, the monohydrochloride, dichydrochloride, monohydrobromide, maleate and methanesulphonate salts of trans-4-{2-[4-(2,3-dichlorophenyl)-piperazine-1-yl]-ethyl}-N,N-dimethylcarbamoyl-cyclohexyl-amine are readily prepared, and may be isolated in high yield and high purity. These salts possess suitable solubility, handling and stability characteristics for use in pharmaceutical compositions. Trans-4-{2-[4-(2,3-dichlorophenyl)-piperazine-1-yl]-ethyl}-N,N-dimethylcarbamoyl-cyclohexyl-amine monohydrochloride is particularly preferred, as in some embodiments it may be prepared in the highest yield and highest purity as compared to the other salts and base form. Another advantage of the monohydrochloride salt is that in some embodiments it can readily be prepared using standard solvents and reaction conditions.

The present invention also relates to pharmaceutical compositions containing the monohydrochloride, dihydrochloride, monohydrobromide, maleate or methanesulphonate salt of trans 4-{2-[4-(2,3-dichlorophenyl)-piperazine-1-yl]-ethyl}-N,N-dimethylcarbamoyl-cyclohexylamine and/or hydrates and/or solvates thereof, and a pharmaceutically acceptable carrier.

In one embodiment, the present invention relates to pharmaceutical compositions containing trans 4-{2-[4-(2,3-dichlorophenyl)-piperazine-1-yl]-ethyl}-N,N-dimethylcarbamoyl-cyclohexylamine monohydrochloride, and/or hydrates and/or solvates thereof, for example trans 4-{2-[4-(2,3-dichlorophenyl)-piperazine-1-yl]-ethyl}-N,N-dimethylcarbamoyl-cyclohexylamine monohydrochloride.

In another embodiment, the present invention relates to pharmaceutical compositions containing trans 4-{2-[4-(2,3-dichlorophenyl)-piperazine-1-yl]-ethyl}-N,N-dimethylcarbamoyl-cyclohexylamine dihydrochloride, and/or hydrates and/or solvates thereof, for example trans 4-{2-[4-(2,3-dichlorophenyl)-piperazine-1-yl]-ethyl}-N,N-dimethylcarbamoyl-cyclohexylamine dihydrochloride.

In a further embodiment, the present invention relates to pharmaceutical compositions containing trans 4-{2-[4-(2,3-dichlorophenyl)-piperazine-1-yl]-ethyl}-N,N-dimethylcarbamoyl-cyclohexylamine monohydrobromide, and/or hydrates and/or solvates thereof, for example trans 4-{2-[4-(2,3-dichlorophenyl)-piperazine-1-yl]-ethyl}-N,N-dimethylcarbamoyl-cyclohexylamine monohydrobromide.

In yet a further embodiment, the present invention relates to pharmaceutical compositions containing trans 4-{2-[4-(2,3-dichlorophenyl)-piperazine-1-yl]-ethyl}-N,N-dimethylcarbamoyl-cyclohexylamine maleate, and/or hydrates and/or solvates thereof, for example trans 4-{2-[4-(2,3-dichlorophenyl)-piperazine-1-yl]-ethyl}-N,N-dimethylcarbamoyl-cyclohexylamine maleate.

In one embodiment, the present invention relates to pharmaceutical compositions containing trans 4-{2-[4-(2,3-dichlorophenyl)-piperazine-1-yl]-ethyl}-N,N-dimethylcarbamoyl-cyclohexylamine methanesulfonate, and/or hydrates and/or solvates thereof, for example trans 4-{2-[4-(2,3-dichlorophenyl)-piperazine-1-yl]-ethyl}-N,N-dimethylcarbamoyl-cyclohexylamine methanesulfonate.

The pharmaceutical compositions may be administered by any convenient method, for example by oral, parenteral, buccal, sublingual, rectal or transdermal administration.

For oral administration the pharmaceutical compositions can be formulated as liquids or solids, for example as syrups, suspensions, emulsions, tablets, capsules and lozenges.

A liquid formulation typically contains a suspension or solution of the active agent in a suitable liquid carrier(s), for example in an aqueous or non-aqueous solvent, such as water, ethanol, glycerol, polyethylene glycol or an oil. The formulation may also contain one or more suspending agents, preservatives, flavourings or colouring agents.

A composition in the solid form of a tablet can be prepared using any suitable pharmaceutical carrier(s) routinely used for preparing solid formulations. Examples of such carriers include magnesium stearate, starch, lactose, sucrose, cellulose, etc.

A composition in the solid form of a capsule can be prepared using routine encapsulation procedures. For example, pellets containing the active agent can be prepared using standard carriers and filled into a hard gelatine capsule. Alternatively, a dispersion or suspension can be prepared using any suitable pharmaceutical carrier(s), for example aqueous gums, celluloses, silicates or oils and the dispersion or suspension then filled into a soft gelatine capsule.

Typical parenteral compositions contain the active agent in a sterile aqueous carrier or parenterally acceptable oil, for example polyethylene glycol, polyvinyl pyrrolidone, lecithin, arachis oil, sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active agent in a physiologically acceptable aqueous or non-aqueous solvent and are usually presented in single quantity or multidose quantities in sterile sealed containers, which can take the form of a cartridge or refill for use with an atomising device. Alternatively, the sealed container may be a unitary dispersing device, such as a single dose nasal inhaler fitted with a metering valve or an aerosol spray which is intended for disposal once the contents of the container have been exhausted. When the dosage form comprises an aerosol spray, it may contain a propellant which can be compressed gas, such as compressed air or an organic propellant, such as a fluorochlorohydrocarbon. The aerosol spray dosage form can also take the form of a pump-atomiser.

Compositions suitable for buccal or sublingual administration include tablets, lozenges and pastilles, wherein the active agent is formulated with a carrier, such as sugar and acacia, tragacanth, or gelatine and glycerol, etc.

Compositions suitable for rectal administration may conveniently be in the form of suppositories containing a conventional suppository base, such as cocoa butter.

Compositions suitable for transdermal administration may include ointments, gels and patches.

Compositions of the present invention are preferably in a unit dose form, such as a tablet, capsule or ampoule.

The present invention also relates to the use of monohydrochloride, dihydrochloride, monohydrobromide, maleate and methanesulphonate salts of trans 4-{2-[4-(2,3-dichlorophenyl)-piperazine-1-yl]-ethyl}-N,N-dimethylcarbamoyl-cyclohexylamine, and/or hydrates and/or solvates thereof, in the manufacture of medicaments to treat and/or prevent conditions which require modulation of dopamine receptors, such as dopamine $D_3$ and/or $D_2$ receptors.

In yet a further aspect, the present invention provides methods of treating conditions which require modulation of dopamine receptors, such as dopamine $D_3$ and/or $D_2$ receptors, comprising administering to a subject in need thereof an effective amount of the monohydrochloride, dihydrochloride, monohydrobromide, maleate and/or methanesulphonate salt of trans 4-{2-[4-(2,3-dichlorophenyl)-piperazine-1-yl]-ethyl}-N,N-dimethylcarbamoyl-cyclohexylamine, and/or hydrates and/or solvates thereof.

In one embodiment, the present invention relates to methods of treatment comprising administering trans 4-{2-[4-(2,3-dichlorophenyl)-piperazine-1-yl]-ethyl}-N,N-dimethylcarbamoyl-cyclohexylamine monohydrochloride, and/or hydrates and/or solvates thereof, for example trans 4-{2-[4-(2,3-dichlorophenyl)-piperazine-1-yl]-ethyl}-N,N-dimethylcarbamoyl-cyclohexylamine monohydrochloride.

In another embodiment, the present invention relates to methods of treatment comprising administering trans 4-{2-[4-(2,3-dichlorophenyl)-piperazine-1-yl]-ethyl}-N,N-dimethylcarbamoyl-cyclohexylamine dihydrochloride, and/or hydrates and/or solvates thereof, for example trans 4-{2-[4-(2,3-dichlorophenyl)-piperazine-1-yl]-ethyl}-N,N-dimethylcarbamoyl-cyclohexylamine dihydrochloride.

In a further embodiment, the present invention relates methods of treatment comprising administering trans 4-{2-[4-(2,3-dichlorophenyl)-piperazine-1-yl]-ethyl}-N,N-dimethylcarbamoyl-cyclohexylamine monohydrobromide, and/or hydrates and/or solvates thereof, for example trans 4-{2-[4-(2,3-dichlorophenyl)-piperazine-1-yl]-ethyl}-N,N-dimethylcarbamoyl-cyclohexylamine monohydrobromide.

In yet a further embodiment, the present invention relates methods of treatment comprising administering trans 4-{2-[4-(2,3-dichlorophenyl)-piperazine-1-yl]-ethyl}-N,N-dimethylcarbamoyl-cyclohexylamine maleate, and/or hydrates and/or solvates thereof, for example trans 4-{2-[4-(2,3-dichlorophenyl)-piperazine-1-yl]-ethyl}-N,N-dimethylcarbamoyl-cyclohexylamine maleate.

In one embodiment, the present invention relates to methods of treatment comprising administering trans 4-{2-[4-(2,3-dichlorophenyl)-piperazine-1-yl]-ethyl}-N,N-dimethylcarbamoyl-cyclohexylamine methanesulfonate, and/or hydrates and/or solvates thereof, for example trans 4-{2-[4-(2,3-dichlorophenyl)-piperazine-1-yl]-ethyl}-N,N-dimethylcarbamoyl-cyclohexylamine methanesulfonate.

Dysfunction of the dopaminergic neurotransmitter system can be observed in the pathology of several neuropsychiatric disorders such as schizophrenia, Parkinson's disease and the drug abuse. The effect of dopamine is mediated via at least five distinct dopamine receptors belonging to $D_1$—(i.e. $D_1$ and $D_5$), or $D_2$—(i.e. $D_2$, $D_3$ and $D_4$) receptor families. $D_3$ receptors have been shown to have characteristic distribution in the central dopaninergic systems. Namely, they were found in high densities in certain limbic structures, such as nucleus accumbens and islands of Calleya. Therefore, selective modulation of $D_3$ receptors may be a promising approach for more selective modulation of the dopaminerg functions and consequently offers successful therapeutic interventions in several abnormalities such as schizophrenia, emotional or cognitive dysfunctions (Sokoloff, P. et al: Nature, 1990, 347, 146; Schwartz, J.-C. et al.: Clin. Neuropharmacol., 1993, 16, 295; Levant, B.: Pharmacol. Rev., 1997, 49, 231), drug abuse (Pilla, C. et al: Nature, 1999, 400, 371) and Parkinson's disease (Levant, B. et al.: CNS Drugs, 1999, 12, 391) or pain (Levant, B. et al.: Neurosci. Lett., 2001, 303, 9).

The dopamine $D_2$ receptors are widely distributed in the brain and are known to be involved in numerous physiological functions and pathological states. Dopamine $D_2$ antagonists are for example used as antipsychotic agents. However, it is also well known that massive antagonism of the $D_2$ receptors leads to unwanted side effects, such as extrapyramidal motor symptoms, psychomotor sedation, or cognitive blunting. These side effects seriously restrict the therapeutic utilization of $D_2$ antagonists (Wong A. H. C. et al.: Neurosci. Biobehav. Rev. 2003, 27, 269).

Conditions which require modulation of dopamine $D_3$ and/or dopamine $D_2$ receptors include, but are not limited to, psychotic states (e.g. schizophrenia, schizo-affective disorders), cognitive impairment accompanying schizophrenia, mild-to moderate cognitive deficits, dementia, psychotic states associated with dementia, psychotic depression, mania, acute mania, bipolar disorder, paranoid and delusional disorders, dyskinetic disorders (e.g. Parkinson's disease), neuroleptic induced parkinsonism, tardive dyskinesia, eating disorders (e.g. bulimia nervosa), attention deficit disorders, infantile hyperactivity disorders, anxiety, sexual functional disorders, sleeping disorder, emesis, aggression, autism and drug abuse.

In exemplary embodiments, the present invention relates to methods of treating schizophrenia, schizo-affective disorders, cognitive impairment accompanying schizophrenia, mild-to moderate cognitive deficits, dementia, psychotic states associated with dementia, psychotic depression, mania, acute mania, bipolar disorder, paranoid and delusional disorders, dyskinetic disorders (e.g. Parkinson's disease), neuroleptic induced parkinsonism, depression, anxiety and drug abuse (e.g. cocaine, alcohol, nicotine abuse).

The particular combination of the two receptor-actions described above allows the simultaneous manifestations of the actions of $D_3$ functional antagonism (e.g. cognitive enhancer effect, inhibition of extrapyramidal motor symptoms, inhibitory action on drug abuse (and that of the $D_2$ functional antagonisms (e.g. antipsychotic effect). Furthermore, the same combination surprisingly results in cancelling the disadvantageous features of $D_2$ antagonism (e.g. extrapyramidal symptoms, psychomotor sedation and cognitive disturbances).

DEFINITIONS

The term "pharmaceutically acceptable" means biologically or pharmacologically compatible for in vivo use in animals or humans, and preferably means approved by a regulatory agency of the Federal or a state government or listed in the U.S. Pharmacopeia or other generally recognized pharmacopeia for use in animals, and more particularly in humans.

The term "schizophrenia" is intended to include the group of mental disorders characterized by disruptions in thinking and perception, and includes schizophrenia (and all its subtypes; paranoid, catatonic, disorganized, residual, undifferentiated) and other psychotic disorders (as per Diagnostic and Statistical Manual for Mental Disorders, Fourth Edition, Washington, D.C. (1994): American Psychiatric Association, or The ICD-10 Classification of Mental and Behavioural Disorders: Clinical Descriptions and Diagnostic Guidelines, Geneva (1992): World Health Organization) such as schizophreniform and schizoaffective disorders, brief psychotic disorder, etc.

In a clinical evaluation, schizophrenia is commonly marked by "positive symptoms" such as hallucinations (especially auditory hallucination which are usually experienced as voices), disorganized thought processes and delusions as well as "negative symptoms" which include affective flattening, alogia, avolition, and anhedonia.

The term "the negative symptoms of schizophrenia" refer to a class of symptoms of schizophrenia which can be considered to reflect a 'loss' in functional, directed thought or activity. Negative symptoms of schizophrenia are well known in the art, and include affective flattening (characterized by, for example, an immobile and/or unresponsive facial expression, poor eye contact and reduced body language), alogia ('poverty of speech' or brief, laconic and/or empty replies), avolition (characterized by a reduced or absent ability to initiate and carry out goal-directed activities), anhedonia (loss of interest or pleasure), asocialty (reduced social drive and interaction), apathy and other negative symptoms known to those of skill in the art. The negative symptoms of schizophrenia may be assessed using any methodology known in the art including, but not limited to, the Brief Psychiatric Rating Scale (BPRS), and the Positive and Negative Symptom Scale (PANSS). The BPRS and PANSS have subscales or factors that can be used to measure negative symptoms. Other scales have been designed to address specifically negative symptoms: For example the Scale for the Assessment of Negative Symptoms (SANS), the Negative Symptoms Assessment (NSA) and the Schedule for the Deficit Syndrome (SDS). Subscales of the BPRS and PANSS may also be used to assess positive symptoms, although methods for specifically assessing positive symptoms are also available (e.g., the Scale for the Assessment of Positive Symptoms, or SAPS).

The term "cognitive deficits associated with schizophrenia" refers to cognitive deficits in schizophrenia patients. Cognitive impairment in schizophrenia is a core feature of the illness (i.e. not a result of treatment or clinical symptoms). Cognitive deficits include, but are not limited to deficits of attention/vigilance, working memory, verbal learning and memory, visuospatial memory, reasoning/problem solving and social cognition. There are numerous neuropsychological tests used to measure cognitive deficits in schizophrenia, such as the Wisconsin Card Sorting Test (WCST).

The terms "treat," "treatment," and "treating" refer to one or more of the following:
  (a) relieving or alleviating at least one symptom of a disorder in a subject, including for example, allergic and inflammatory disorders, such as asthma and COPD;
  (b) relieving or alleviating the intensity and/or duration of a manifestation of a disorder experienced by a subject including, but not limited to, those that are in response to a given stimulus (e.g., pressure, tissue injury, cold temperature, etc.);
  (c) arresting, delaying the onset (i.e., the period prior to clinical manifestation of a disorder) and/or reducing the risk of developing or worsening a disorder.

An "effective amount" means the amount of an active ingredient that, when administered to a patient (e.g., a mammal) for treating a disease (i.e., schizophrenia), is sufficient to effect such treatment for the disease, or an amount that is sufficient for modulating a dopamine receptor (e.g., the dopamine $D_2$ and/or dopamine $D_3$ receptor) to achieve the objectives of the invention. The "effective amount" will vary depending on the compound, the disease and its severity and the age, weight, responsiveness, etc., of the patient to be treated.

A subject or patient in whom administration of the therapeutic compound is an effective therapeutic regimen for a disease or disorder is preferably a human, but can be any animal, including a laboratory animal in the context of a trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%. Alternatively, particularly with respect to biological systems or processes, the term can mean within an order of magnitude, preferably within 5-fold, and more preferably within 2-fold, of a value. All numbers in the specification are presumed to be modified by the term "about" (even in the absence of such term), unless explicitly stated otherwise.

The following examples are merely illustrative of the present invention and should not be construed as limiting the scope of the invention in any way as many variations and equivalents that are encompassed by the present invention will become apparent to those skilled in the an upon reading the present disclosure.

EXAMPLE 1

Trans 4-{2-[4-(2,3-dichlorophenyl)-piperazine-1-yl]-ethyl}-N,N-dimethylcarbamoyl-cyclohexylamine methanesulfonate 3.0 g (0.007 mol) of trans 4-{2-[4-(2,3-dichlorophenyl)-piperazine-1-yl]-ethyl}-N,N-dimethylcarbamoyl-cyclohexylamine and 0.46 ml (0.007 mol) of methanesulfonic acid were mixed in a mixture of 10 ml methanol and 80 ml acetonitrile. The reaction mixture was heated to boiling temperature and the homogenous solution obtained was concentrated to 25 ml by distillation. The resulting suspension was then stirred at a temperature of from 0-5° C. for 2 hours and the product was isolated by filtration to afford 3.1 g (84%) of trans 4-{2-[4-(2,3-dichlorophenyl)-piperazine-1-yl]-ethyl}-N,N-dimethylcarbamoyl-cyclohexylamine methanesulfonate. Melting point: 225-229° C.

EXAMPLE 2

Trans 4-{2-[4-(2,3-dichlorophenyl)-piperazine-1-yl]-ethyl}-N,N-dimethylcarbamoyl-cyclohexylamine maleate 3.0 g (0.007 mol) of trans 4-{2-[4-(2,3-dichlorophenyl)-piperazine-1-yl]-ethyl}-N,N-dimethylcarbamoyl-cyclohexylamine and 0.83 g (0.007 mol) of maleic acid were suspended in 150 ml of acetone. The reaction mixture was heated to boiling temperature and stirred for half an hour, then concentrated to 25 ml by distillation. The resulting suspension was stirred at a temperature of from 0-5° C. for 2 hours and the product obtained was isolated by filtration to afford 3.14 g (82%) of trans 4-{2-[4-(2,3-dichlorophenyl)-piperazine-1-yl]-ethyl}-N,N-dimethylcarbamoyl-cyclohexylamine maleate. Melting point: 173-177° C.

EXAMPLE 3

Trans 4-{2-[4-(2,3-dichlorophenyl)-piperazine-1-yl]-ethyl}-N,N-dimethylcarbamoyl-cyclohexylamine hydrobromide 3.0 g (0.007 mol) of trans 4-{2-[4-(2,3-dichlorophenyl)-piperazine-1-yl]-ethyl}-N,N-dimethylcarbamoyl-cyclohexylamine was suspended in a mixture of 12 ml of methanol and 38 ml (1.5%) of hydrogen bromide solution. The reaction mixture was heated to boiling temperature and the homogenous solution obtained was cooled to a temperature of from 0-5° C. for 1 hour and further stirred at this temperature for 2 hours. The product obtained was isolated by filtration to afford 3.0 g (85%) of Trans 4-{2-[4-(2,3-dichlorophenyl)-piperazine-1-yl]-ethyl}-N,N-dimethylcarbamoyl-cyclohexylamine hydrobromide. Melting point: 248-252° C.

EXAMPLE 4

Trans 4-{2-[4-(2,3-dichlorophenyl)-piperazine-1-yl]-ethyl}-N,N-dimethylcarbamoyl-cyclohexylamine dihydrochloride 3.0 g (0.007 mol) of trans 4-{2-[4-(2,3-dichlorophenyl)-piperazine-1-yl]-ethyl}-N,N-dimethylcarbamoyl-cyclohexylamine was suspended in 70 ml (20.5 g/100 ml) of anhydrous methanol saturated with hydrogen chloride. The reaction mixture was heated to boiling temperature and the resulting homogenous solution was concentrated to 25 ml by distillation. The resulting suspension was stirred at a temperature of from 20-25° C. for 2 hours and the product was isolated by filtration to afford 3.0 g (85%) of trans 4-{2-[4-(2,3-dichlorophenyl)-piperazine-1-yl]-ethyl}-N,N-dimethylcarbamoyl-cyclohexylamine dihydrochloride. Melting point: 216-220° C.

EXAMPLE 5

Trans 4-{2-[4-(2,3-dichlorophenyl)-piperazine-1-yl]-ethyl}-N,N-dimethylcarbamoyl-cyclohexylamine monohydrochloride 42.75 g (0.1 mol) of trans 4-{2-[4-(2,3-dichlorophenyl)-piperazine-1-yl]-ethyl}-N,N-dimethylcarbamoyl-cyclohexylamine was suspended in a mixture of 90 ml methanol and 350 ml of distilled water. A solution of 10.7 g (0.2 mol) of ammonium chloride in 50 ml of water was then added. The reaction mixture was stirred at a temperature of from 60-75° C. for about 4 hours then 15-20 ml solvent was removed by distillation. The reaction mixture was cooled to a temperature of from 20-30° C. for 1 hour then further cooled to a temperature of from 0-10° C. and stirred for another 3 hours. The resulting precipitate was isolated by filtration and washed with water to afford 43.6 g (94%) of trans 4-{2-[4-(2,3-dichlorophenyl)-piperazine-1-yl]-ethyl}-N,N-dimethylcarbamoyl-cyclohexylamine monohydrochloride. Melting point: 221-224° C.

EXAMPLE 6

Trans 4-{2-[4-(2,3-dichlorophenyl)-piperazine-1-yl]-ethyl}-N,N-dimethylcarbamoyl-cyclohexylamine monohydrochloride 147.5 g (0.345 mol) of trans 4-{2-[4-(2,3-dichlorophenyl)-piperazine-1-yl]-ethyl}-N,N-dimethylcarbamoyl-cyclohexylamine was suspended in a mixture of 300 ml of methanol and 1200 ml of distilled water. The reaction mixture was heated to a temperature of from 60-75° C. and a mixture of 40 ml (30%) of aqueous hydrogen chloride solution and 32 ml of water was added. The reaction mixture was stirred at a temperature of from 60-75° C. The homogenous solution thus obtained was cooled to a temperature of from 20-30° C. for 1 hour then further cooled to a temperature of from 0-10° C. and stirred at this temperature for 3 hours. The resulting precipitate was isolated by filtration and washed with water to afford 152.9 g (95%) of trans 4-{2-[4-(2,3-dichlorophenyl)-piperazine-1-yl]-ethyl}-N,N-dimethylcarbamoyl-cyclohexylamine monohydrochloride. Melting point: 221-224° C.

The characterization of trans 4-{2-[4-(2,3-dichlorophenyl)-piperazine-1-yl]-ethyl}-N,N-dimethylcarbamoyl-cyclohexylamine monohydrochloride was carried out by thermogravimetric (TG), differential scanning colorimetric (DSC), infrared spectroscopic (FT-IR), Raman spectroscopic (FT-Raman) and powder X-ray diffraction (PXRD) solid phase analytical methods.

Trans 4-{2-[4-(2,3-dichlorophenyl)-piperazine-1-yl]-ethyl}-N,N-dimethylcarbamoyl-cyclohexylamine monohydrochloride salt was identified as a solvent-free and anhydrous form, which exhibits satisfactory thermal stability up to about 200° C. Trans 4-{2-[4-(2,3-dichlorophenyl)-piperazine-1-yl]-ethyl}-N,N-dimethylcarbamoyl-cyclohexylamine monohydrochloride melts above 220° C., with accompanying vigorous thermal decomposition and high weight loss (see FIGS. 4 and 5).

Parameters for solid phase analytical methods used are as follows:

| FT-IR Spectroscopy | |
|---|---|
| Type of apparatus: | Thermo-Nicolet 6700 |
| Phase (solvent): | KBr |
| Spectral resolution | 4 cm$^{-1}$ |
| Scan-number: | 100 |

| FT-Raman Spectroscopy | |
|---|---|
| Type of apparatus: | Thermo-Nicolet NXR9650 |
| Measuring range: | 3500-200 cm$^{-1}$ |
| Spectral resolution: | 4 cm$^{-1}$ |
| Scan-number: | 128 |
| Laser performance: | 300 mW |

| Powder X-ray Diffraction | |
|---|---|
| Type of apparatus: | PANanalytical X'Pert PRO |
| Radiation: | CuK$_\alpha$ |
| Accelerating potential: | 40 kV |
| Anode current: | 40 mA |
| Goniometer: | PW3050/60 |
| Exposure speed: | 0.208 °2θ/s |
| Sample container: | Spinner PW3064 |
| Rotational speed of sample container: | 1 turn/s |
| Uncertainty of 2θ measurement: | ±0.2° |

| TG Analysis | |
|---|---|
| Type of apparatus: | TA Instruments TGA Q50 |
| Heating speed: | 10° C./min |
| Sample weight: | ~5-10 mg |
| Atmosphere: | 60 ml/min N$_2$ |

| DSC Analysis | |
|---|---|
| Type of apparatus: | TA Instruments DSC Q10 |
| Heating speed: | 10° C./min |
| Sample weight: | ~1-2 mg |
| Pot type: | opened |
| Atmosphere: | 50 ml/min N$_2$ |

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure.

The depicted and described embodiments of the invention are exemplary only, and are not exhaustive of the scope of the invention. Consequently, the invention is intended to be limited only by the spirit and scope of the appended claims, giving full cognizance to equivalence in all respects.

All references cited herein are hereby incorporated by reference in their entirety.

What is claimed is:

1. Trans 4-{2-[4-(2,3-dichlorophenyl)-piperazine-1-yl]-ethyl}-N,N-dimethylcarbamoyl-cyclohexylamine monohydrochloride, and hydrates and solvates thereof.

2. Crystalline trans 4-{2-[4-(2,3-dichlorophenyl)-piperazine-1-yl]-ethyl}-N,N-dimethylcarbamoyl-cyclohexylamine hydrochloride having a powder X-ray diffraction pattern that comprises peaks at about 6.6, about 7.3, about 13.2, about 21.1, and about 22.4, each about ±0.2 degrees 2θ.

3. The crystalline form of claim 2, wherein the powder X-ray diffraction pattern further comprises peaks at about 14.2, about 14.6, about 16.9, about 24.8, about 26.5 and about 26.6°, each about ±0.2 degrees 2θ.

4. The crystalline form of claim 2, having an infrared spectrum comprising characteristic peaks at about 3321, about 2914, about 1652, about 1526, about 956, and about 784 cm$^{-1}$, each about ±4 cm$^{-1}$.

5. The crystalline form of claim 4, wherein the infrared spectrum further comprises characteristic peaks at about 2931, about 2466, and about 715 cm$^{-1}$, each about ±4 cm$^{-1}$.

6. The crystalline form of claim 2, having a Raman spectrum comprising characteristic peaks at about 2969, about 2933, about 2850, about 1578, about 1052, and about 475 cm$^{-1}$, each about ±4 cm$^{-1}$.

7. The crystalline form of claim 6, wherein the Raman spectrum further comprises characteristic peaks at about 3070, about 2986, about 2914, about 2864, and about 1458 cm$^{-1}$, each about ±4 cm$^{-1}$.

8. Trans 4-{2-[4-(2,3-dichlorophenyl)-piperazine-1-yl]-ethyl}-N,N-dimethylcarbamoyl-cyclohexylamine dihydrochloride, and hydrates and solvates thereof.

9. Trans 4-{2-[4-(2,3-dichlorophenyl)-piperazine-1-yl]-ethyl}-N,N-dimethylcarbamoyl-cyclohexylamine monohydrobromide, and hydrates and solvates thereof.

10. Trans 4-{2-[4-(2,3-dichlorophenyl)-piperazine-1-yl]-ethyl}-N,N-dimethylcarbamoyl-cyclohexylamine maleate, and hydrates and solvates thereof.

11. Trans 4-{2-[4-(2,3-dichlorophenyl)-piperazine-1-yl]-ethyl}-N,N-dimethylcarbamoyl-cyclohexylamine methanesulphonate, and hydrates and solvates thereof.

12. A process for preparing a compound chosen from monohydrochloride, dihydrochloride, monohydrobromide, maleate, and methanesulphonate salts, hydrates, and solvates of trans 4-{2-[4-(2,3-dichlorophenyl)-piperazine-1-yl]-ethyl}-N,N-dimethylcarbamoyl-cyclohexylamine, comprising (i) adding trans 4-{2-[4-(2,3-dichlorophenyl)-piperazine-1-yl]-ethyl}-N,N-dimethylcarbamoyl-cyclohexylamine to a solvent or mixture of solvents, (ii) adding hydrochloric acid, or a salt thereof prepared from a base which is weaker base than the trans 4-{2-[4-(2,3-dichlorophenyl)-piperazine-1-yl]-ethyl}-N,N-dimethylcarbamoyl-cyclohexylamine, or a solution thereof, to the mixture formed in step(i), and (iii) optionally isolating the compound.

13. A process for preparing trans 4-{2-[4-(2,3-dichlorophenyl)-piperazine-1-yl]-ethyl}-N,N-dimethylcarbamoyl-cyclohexylamine dihydrochloride, and hydrates and solvates thereof, comprising (i) adding trans 4-{2-[4-(2,3-dichlorophenyl)-piperazine-1-yl]-ethyl}-N,N-dimethylcarbamoyl-cyclohexylamine to a solvent or mixture of solvents, (ii) adding hydrochloric acid, or a salt thereof prepared from a base which is weaker base than the trans 4-{2-[4-(2,3-dichlorophenyl)-piperazine-1-yl]-ethyl}-N,N-dimethylcarbamoyl-cyclohexylamine, or a solution thereof, to the mixture formed in step (i), and (iii) optionally isolating the compound.

14. A process for preparing Trans 4-{2-[4-(2,3-dichlorophenyl)-piperazine-1-yl]-ethyl}-N,N-dimethyl carbamoyl-cyclohexylamine monohydrobromide, and hydrates and solvates thereof, comprising (i) adding trans 4-{2-[4-(2,3-dichlorophenyl)-piperazine-1-yl]-ethyl}-N,N-dimethylcarbamoyl-cyclohexylamine to a solvent or mixture of solvents, (ii) adding hydrobromic acid, or a salt thereof prepared from a base which is weaker base than the trans 4-{2-[4-(2,3-dichlorophenyl)-piperazine-1-yl]-ethyl}-N,N-dimethylcarbamoyl-cyclohexylamine, or a solution thereof, to the mixture formed in step(i), and (iii) optionally isolating the compound.

15. A process for preparing trans 4-{2-[4-(2,3-dichlorophenyl)-piperazine-1-yl]-ethyl}-N,N-dimethylcarbamoyl-cyclohexylamine maleate, and hydrates and solvates thereof, comprising (i) adding trans 4-{2-[4-(2,3-dichlorophenyl)-piperazine-1-yl]-ethyl}-N,N-dimethylcarbamoyl-cyclohexylamine to a solvent or mixture of solvents, (ii) adding maleic acid, or a salt thereof prepared from a base which is weaker base than the trans 4-{2-[4-(2,3-dichlorophenyl)-piperazine-1-yl]-ethyl}-N,N-dimethylcarbamoyl-cyclohexylamine, or a solution thereof, to the mixture formed in step (i), and (iii) optionally isolating the compound.

16. A process for preparing trans 4-{2-[4(2,3-dichlorophenyl)-piperazine-1-yl]-ethyl}-N,N-dimethylcarbamoyl-cyclohexylamine methanesulphonate, and hydrates and solvates thereof, comprising (i) adding trans 4-{2-[4-(2,3dichlorophenyl)-piperazine-1-yl]-ethyl}-N,N-dimethylcarbamoyl-cyclohexylamine to a solvent or mixture of solvents, (ii) adding methanesulfonic acid, or a salt thereof prepared from a base which is weaker base than the trans 4-{2-[4-(2,3-dichlorophenyl)-piperazine-1-yl]-ethyl}-N,N-dimethylcarbamoyl-cyclohexylamine, or a solution thereof, to the mixture formed in step (i), and (iii) optionally isolating the compound.

17. A pharmaceutical composition comprising a compound chosen from monohydrochloride, dihydrochloride, monohydrobromide, maleate, and methanesulphonate salts, hydrates, and solvates of trans 4-{2-[4-(2,3-dichlorophenyl)-piperazine-1-yl]-ethyl}-N,N-dimethylcarbamoyl-cyclohexylamine and a pharmaceutically acceptable carrier.

* * * * *

UNITED STATES PATENT AND TRADEMARK OFFICE
CERTIFICATE OF CORRECTION

PATENT NO. : 7,943,621 B2
APPLICATION NO. : 12/118437
DATED : May 17, 2011
INVENTOR(S) : Laszlo Czibula It is certified that error appears in the above-identified patent and that said Letters Patent is hereby corrected as shown below:

Title Page, please insert

--(30)   Foreign Application Priority Data

May 11, 2007 (HU) ....................   P0700339--.

Signed and Sealed this
Eighth Day of May, 2012

David J. Kappos
*Director of the United States Patent and Trademark Office*